United States Patent [19]
Palti et al.

[11] Patent Number: 5,624,454
[45] Date of Patent: Apr. 29, 1997

[54] PADDED VASCULAR CLAMP

[76] Inventors: Yoram Palti, 51 Ruth St., Haifa, Israel, 34404; Robert Schnall, 5 Hadasna St., Kiryat Bialik, Israel

[21] Appl. No.: 509,203

[22] Filed: Jul. 31, 1995

[30] Foreign Application Priority Data

Jul. 31, 1994 [IL] Israel ......................... 110517

[51] Int. Cl.$^6$ .................................... A61B 17/04
[52] U.S. Cl. .................. 606/151; 606/151; 606/158; 606/207
[58] Field of Search ................ 606/151, 153, 606/207, 157, 158

[56] References Cited

U.S. PATENT DOCUMENTS

| | | | |
|---|---|---|---|
| 3,258,012 | 6/1966 | Nakayama et al. | 606/153 |
| 3,265,069 | 8/1966 | Healey et al. | 606/153 |
| 3,503,398 | 3/1970 | Fogarty et al. | 606/207 |
| 4,531,519 | 7/1985 | Dunn et al. | |
| 5,152,770 | 10/1992 | Bengmark et al. | 606/157 |
| 5,236,437 | 8/1993 | Wilk et al. | 606/207 |
| 5,282,812 | 2/1994 | Suarez Jr. | 606/151 |
| 5,391,181 | 2/1995 | Johnson et al. | 606/207 |

FOREIGN PATENT DOCUMENTS

| | | | |
|---|---|---|---|
| 1103119 | 6/1981 | Canada. | |
| 214727 | 10/1909 | Germany | 606/207 |

*Primary Examiner*—Gary Jackson
*Attorney, Agent, or Firm*—David M. Klein; Bryan Cave LLP

[57] ABSTRACT

A vascular clamp for occluding a blood vessel or duct in a human or animal. The vascular clamp includes a pair of pivoting arms, with a clamping jaw rigidly attached to a distal end of each pivoting arm. A concave substantially semi-cylindrical chamber is formed in each clamping jaw. The clamping jaws are movable between an open position and a closed position, and are aligned so as to form a substantially cylindrical chamber in the closed position. A balloon is mounted in the concave semi-cylindrical chamber of each clamping jaw. Each balloon includes a substantially semi-cylindrical rigid shell conforming to the concave semi-cylindrical chamber and a thin, elastic material pre-filled with a liquid or gaseous fluid at a predetermined pressure. The balloons are configured to completely surround and occlude the blood vessel or duct in the closed position of the vascular clamp. The rigid shell of each balloon is attached to its associated clamping jaw.

11 Claims, 3 Drawing Sheets

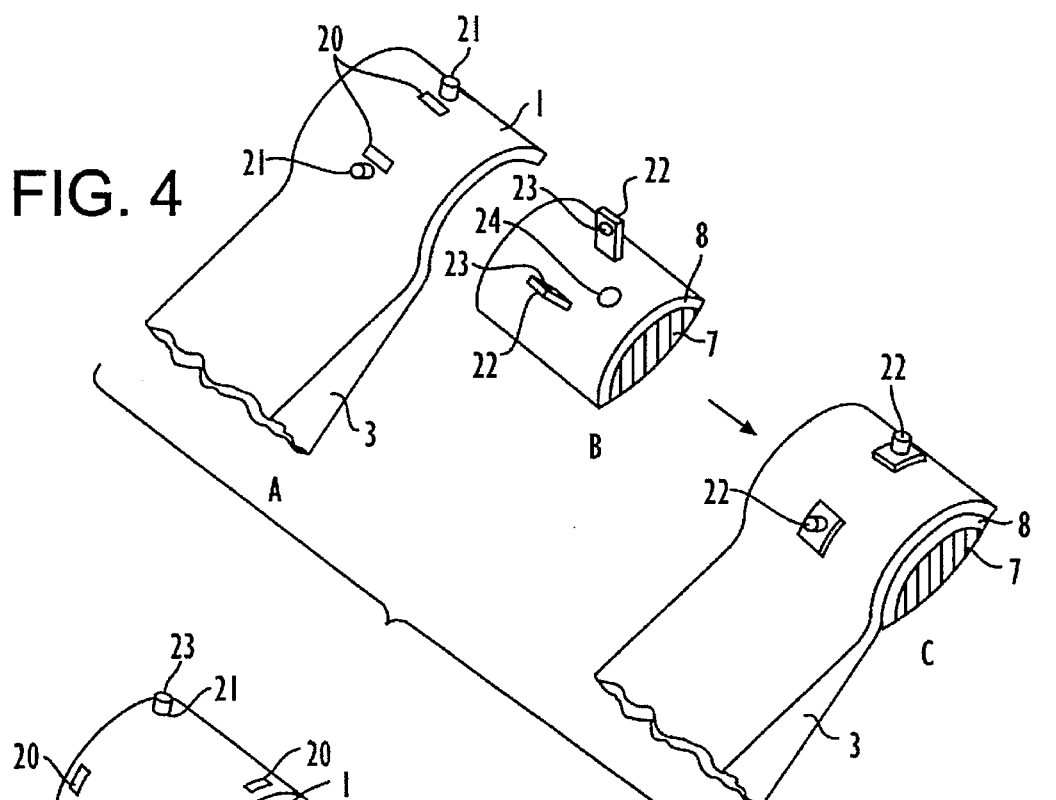
FIG. 4
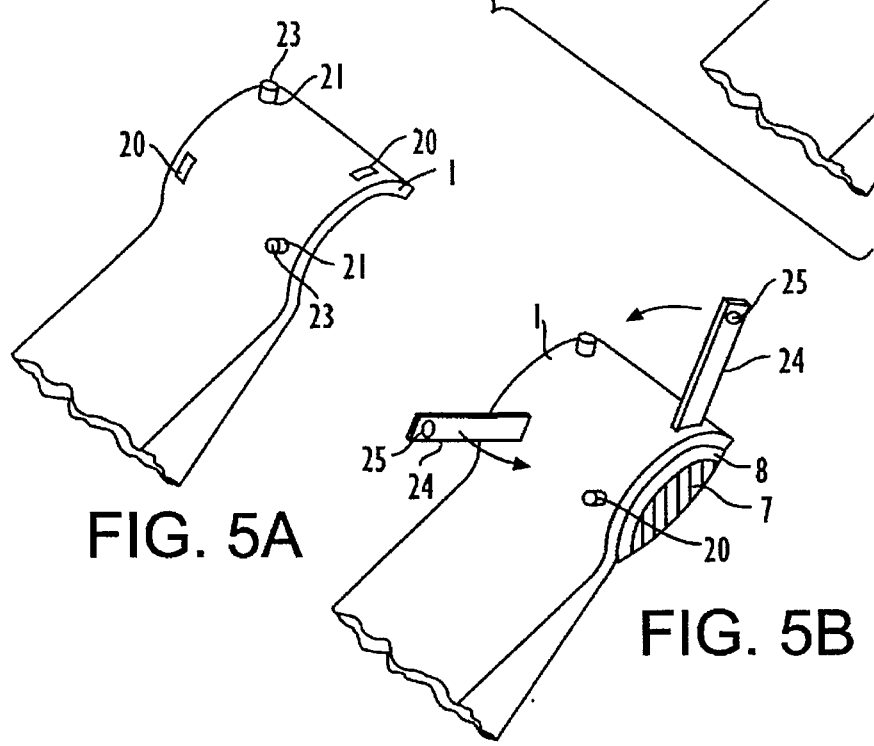
FIG. 5A
FIG. 5B
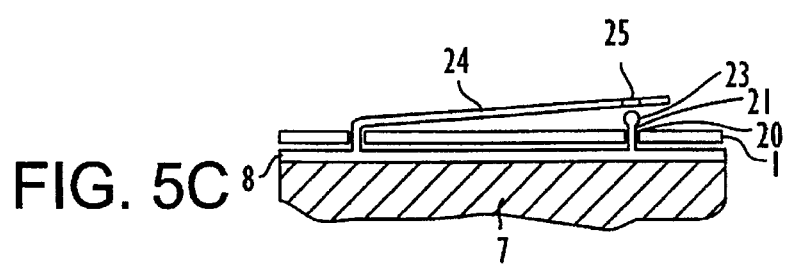
FIG. 5C

PADDED VASCULAR CLAMP

The invention relates to a vascular clamp, particularly to a vascular clamp designed to completely occlude a blood vessel without, however, causing any injury to this vessel.

BACKGROUND OF THE INVENTION

Vascular clamps play a vital and obvious role during surgery, their task being complete vascular occlusion by squeezing the blood vessel between the two jaws of a clamp or a forceps. The process of clamping generates loci of extremely high pressure far in excess of the pressure in the blood vessel itself and are apt to cause serious injury to all layers of the vessel. The generally used clamps such as the Fogarty Clamp, the De Bakey "Atraugrip", the Bulldog Clamp, or Pott's and Satinsky's peripheral vascular clamps exert very high pressures, of up to 9 bar, on the clamped blood vessel and have caused intimal to major medial damage commencing at a pressure of 2.5 bar.

The clinical consequences of vascular injury have not always received sufficient attention, but a few fatal outcomes have been reported which were actually due to clamp injuries. Less obvious damage may cause the eventual attrition of blood vessels by an injury sufficient to cause endothelial desquamation associated with fragmentation of the internal elastic lamina and smooth muscle hyperplasia in the media and formation of an intimal thickening or fibrous plaque.

Clamp-induced damage may have dire consequences to the patient, an important case being that of the early and intermediate fate of aorta-coronary by-pass surgery using reversed saphenous vein. About 150,000 such operations are performed annually in the U.S.A. alone, and the results show an attrition rate of from 5 to 10% for the first year, mainly attributed to thrombosis, 2% per annum during the next six years, associated with intinal hyerplasia due to vascular damage, and 5% per annum for the following 5 years. Thus, even in elite institutions as much as 24% of by-pass surgery may fail owing to iatrogenic vascular damage caused by trauma inflicted during the operation.

In view of the fact that systemic blood pressure is at least one order of magnitude lower than the pressure applied to the blood vessel by the conventional clamps, it becomes evident that vascular occlusion could be achieved at far lower pressures than hitherto applied. An appropriate method of properly blocking the blood flow in a vessel while avoiding localized loci of excessive pressure would be to surround the blood vessel with a uniform external pressure field, analogous to the way in which a blood pressure cuff works.

In recent years it has been tried to replace the rigid and hard clamp surfaces by bodies of soft and resilient material, but those known at present are not feasible for forming an eternal uniform pressure field around the blood vessel, which is the foremost aim of the present invention. These clamps show a certain improvement over the conventional rigid and hard clamps, but all suffer from the drawback that they do not exert uniform, relatively low pressure on the entire circumference of the blood vessel. A few examples are given in the following:

U.S. Pat. No. 4,531,519 (DUNN) discloses a vascular clamp in the form of a tapering, flexible and tubular envelope which is wound around the blood vessel to be occluded and is inflated by air or another fluid.

U.S. Pat. No. 5,152,770 (BENGMARK) describes a similar device which includes a flexible, elongate strip covered on its one side with a plurality of communicating bulbs. The strip is wound around the blood vessel or duct to be occluded and the bulbs are inflated to a pressure serving to occlude the duct. After deflation of the bulbs the strip is removed to allow the duct to re-open. As in the vascular clamp escibed in DUNN, the application of the strip or envelope by winding it around the blood vessel and subsequently inflating it until the flow of blood or other body fluid is stopped, is a difficult and time consuming task. For this reason both devices are used in exceptional cases only.

U.S. Pat. No. 5,282,812 (SUAREZ) discloses a vascular clamp in the form of a strip of metal bent into V-shape with its inside surfaces lined with a resilient material. Closing of a vessel is described, whereby the clamp is to be held in a forceps, to be pushed over the vessel to be occluded and pressed onto the vessel, whereafter the forceps is removed. The material of the strip is supposed to keep its shape after removal of the forceps and to maintain the necessary pressure during the operation. The device is provided with means for engaging the forceps jaws after completed surgery for opening the V and for removing the clamp. It is claimed that the strip material would have a positional memory for exerting the necessary pressure after positioning. This would require a different size and material of the device for every size of vessel and blood pressure.

Canadian Patent No.1103119 (MUERMANS) discloses a surgical clamp having two clamping jaws and comprising a soft pad placed over each jaw. Each pad includes two cavities, one of them tightly located over the respective jaw, the second cavity is filled with a fluid or solid and is subsequently sealed. It is claimed that the device clamps the vessel without damage.

In fact the vessel is clamped between two long surfaces which are soft and resilient, but the effect is equal to the squeezing of the vessel from two opposite directions only without exerting uniform pressure on the entire circumference, which is the aim of the present clamp.

In short, the above described clamps do not fulfill the requirements of occlusion of a blood vessel or any other duct in a living body without damaging it, while the objects of the present invention are as follows:

1. a vascular clamp provided with two compliant and stretchable surfaces surrounding the blood vessel on all sides,
2. a vascular clamp exerting a uniform circumferential pressure field,
3. a vascular clamp exerting an invariant pressure on the vessel during the entire operation,
4. a vascular clamp provided with disposable clamping surfaces.

A vascular clamp permitting the exchange of its clamping surfaces to adapt the clamp to different application in respect of specific blood vessels or ducts.

SUMMARY OF THE INVENTION

A preferred embodiment of the vascular clamp of the invention includes a forceps or pair of tongs comprising two pivotally connected arms each arm being provided at its far end with a jaw concavely curved to form a substantially cylindrical space together with the opposite jaw. Each jaw contains, firmly fastened to its concave side, a balloon of a resilient, flexible and stretchable material filled with a fluid, either liquid or gaseous, at a predetermined pressure, the two balloons facing each other in exact oppositional alignment. In surgery the clamp is positioned with the two balloons enclosing the vessel on opposite sides, the arms are urged together to force the two balloons onto the vessel until the flow of blood is stopped, and are held in this position by known securing means such as serrated strips protruding from the two arms and interengaging at any position of the latter.

The two balloons are preferably disposable and exchangeable and are fastened to the jaws by temporary fastening means, a suitable embodiment including one rigid shell each of semi-cylindrical, or similar, shape co-extensive with the inside contour of the jaws. Each shell forms the base of one balloon, and comprises a closable opening for inflating the balloon. The ends of the two shells are brought into close contact upon closure of the clamp, whereby the two shells enclose a space of circular or similar shape which is filled by the two balloons. The opposed stretchable surfaces of the two balloons surround the vessel or duct closely while urging it into flat shape and occluding it. The shells are preferably made of plastic material and are provided with means for releaseably attaching them to the jaws and for securing their position during the entire operation. The balloons, including their shells, are interchangeable and may be made to different specifications in accordance with the size and nature of the duct or vessel to be occluded.

Another embodiment of the vascular clamp includes two curved jaws attached to two arms which are pivotally connected and are urged apart by an interposed strong spring. Each jaw contains an inflated balloon which are placed to both sides of a blood vessel while the arms are compressed against the force of the spring. After release of the arms the spring urges the balloons onto the blood vessel thereby stopping the blood flow. This kind of clamp is preferably made of a plastic material and is either disposable after use, or is adapted for exchange of the balloons and shells, similar to the device described in the foregoing.

BRIEF DESCRIPTION OF THE DRAWINGS

FIGS 4A, 4B, and 4C illustrate a first mode of assembling a balloon to one jaw of a vascular clamp, FIGS. 5A, 5B and 5C illustrate a second mode of fastening a balloon to a jaw.

DETAILED DESCRIPTION OF THE DRAWINGS

Figure 1:
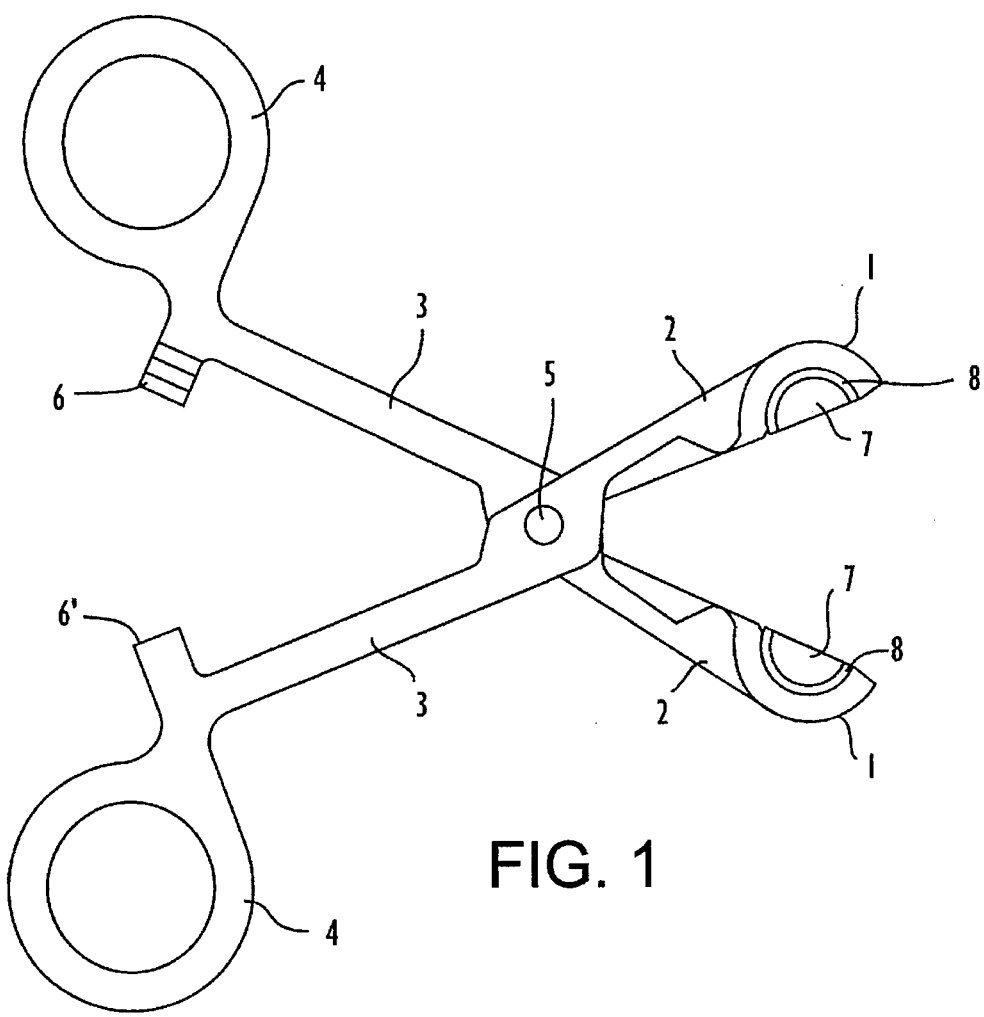
FIG. 1 is a view of a first embodiment of a vascular clamp in open position.
Figure 2:
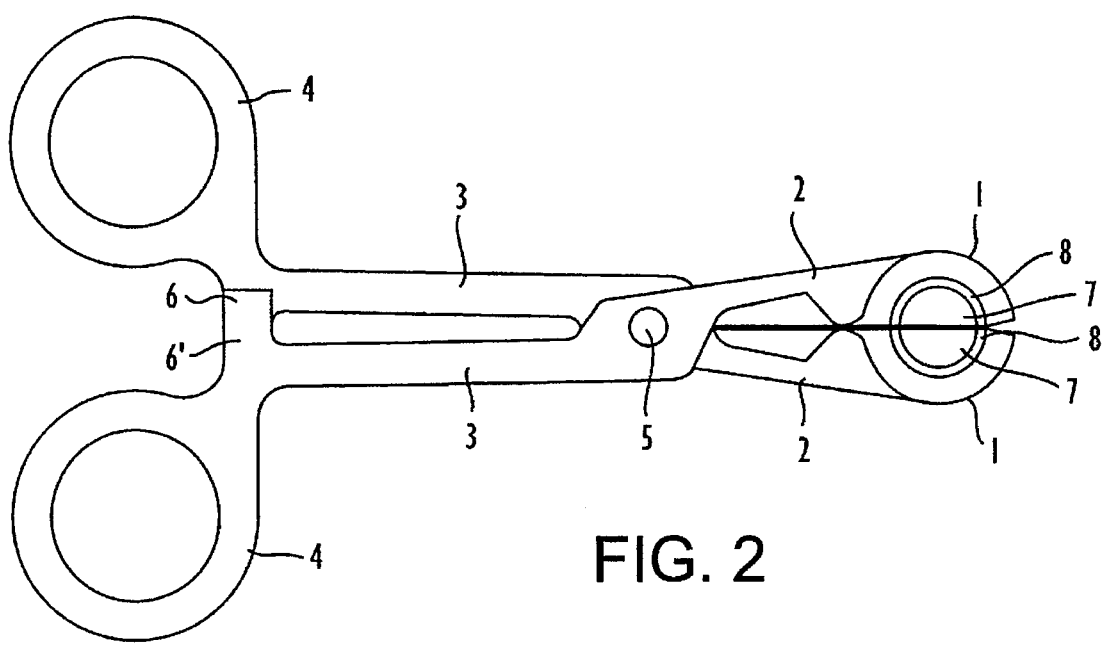
FIG. 2 is a view of the clamp of FIG. 1, in closed position.

With reference to FIGS. 1 and 2, a first embodiment of the vascular clamp of the invention is in the form of a surgical forceps having its originally straight jaws curved in substantially semi-cylindrical shape 1, while reinforcing them against deformation by the addition of backing portions 2. The clamp includes, in a conventional manner, two arms 3 terminating in finger holds 4 and being pivotally interconnected by means of a strong pin 5. The two arms contain serrated lugs 6 and 6' protruding inwardly and facing each other; they serve, again in a conventional manner, to keep the arms and the jaws in the final closed position. One balloon 7 is firmly fastened to the inside of each of the curved jaws 1 by means of a thin shell 8, their shape and design being described with reference to the following drawings. The balloons, in order to be resilient and stretchable, are made of thin sheeting of rubber or a plastic material of similar properties. In closed position, as shown in FIG. 2, they surround the blood vessel on all sides, thus completely occluding it without causing either internal or external damage to the blood vessel.

Figure 3:
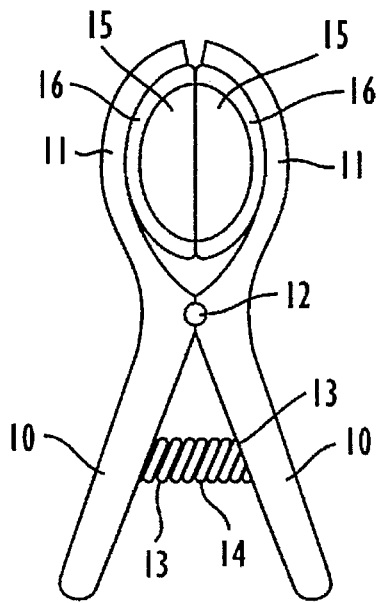
FIG. 3 is a view of a second embodiment of the vascular clamp.

The vascular clamp illustrated in FIG. 3, is preferably manufactured of a plastic material for immediate disposal after one use. It includes two short arms 10 which terminate in two curved jaws 11 and are pivotally interconnected at point 12. The arms comprise two inwardly protruding lugs 13 which support the ends of a strong helical spring 14, configured to urge the two arms apart and to compress the two jaws together. Each jaw contains a balloon 15 firmly attached to it by means of a plastic shell 16, connection between shell and jaw being performed by connecting means known to the art.

One way of connecting a balloon to a jaw of the clamp is illustrated in FIGS. 4A, 4B, and 4C. FIG. 4A shows a curved jaw 1 attached to a reinforced arm 3; the jaw is perforated by two perforations 20 and contains on its outside two outwardly protruding lugs 21. As shown in FIG. 4B, the shell 8 surrounds the balloon 7 firmly and airtightly and includes two outward protruding strips 22 each perforated by a bore 23. The position of the strips is coextensive with that of the perforations 20 in the jaw and after assembly of the shell into the jaw they protrude out of the jaw. The FIG. 4C shows the final stage of assembly, wherein the strips 22 are bent down onto the outer jaw surface and the lugs 21 are placed into the perforations 23, thereby securing the shell firmly in the jaw.

As can be seen from FIG. 4B, the shell is approximately semi-cylindrical, its outside conforms with the inside of the jaw. The balloon material is tightly fastened, preferably glued, to the two ends and the two sides of the shell. The balloon being thereafter inflated by injection of water or air through an opening 24 in the back of the shell. The fluid is preferably injected by means of a syringe which is inserted through opening 24, the latter being firmly closed by glue or putty after withdrawal of the syringe needle.

FIGS. 5A, 5B and 5C show another method of fastening a balloon to the jaw of the clamp: as shown in FIG. 5B the shell 8 holding the balloon 7, is provided with two short outstanding lugs 21 which are thickened at their end in the form of bulbs 23, and with two outstanding strips 24 perforated near their outer ends by holes 25. The position of the strips and the lugs conform with the position of four perforations 20 in the curved jaw 1 (FIG. 5A) of the clamp. In FIG. 5C one lug 21 and one strip 24 are shown to have been pushed through these perforations while the strip 24 is shown to have been bent over towards the lug 21, just before the hole 25 is positioned on the lug, where the bulb will hold the strip in position and thereby fasten the shell and balloon to the jaw.

Figure 6:
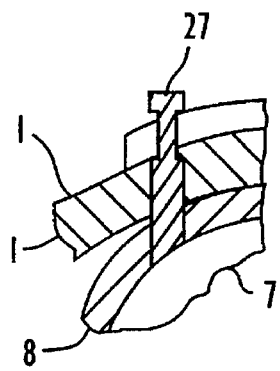
FIGS. 6, 7, and 8 illustrate a third mode of fastening a balloon to a jaw.
Figure 7:
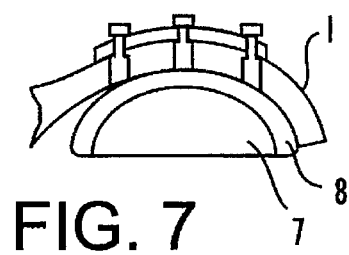
Figure 8:
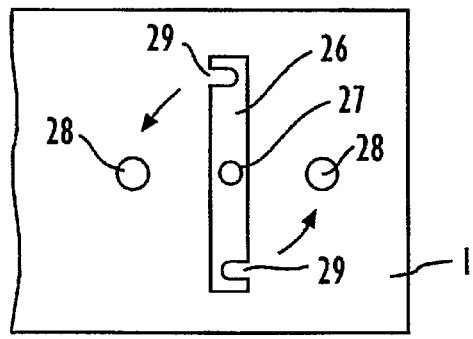

Still another method of fastening the shell and balloon to the jaw is shown in FIGS. 6, 7, and 8: Herein the jaw 1 is perforated in three places, permitting the insertion of two lugs 28 and one central pivot pin 27 therethrough. The central pivot 27 carries a lever 26 which is configured to rotated about the pivot and to engage the two lugs 28 by means of two recesses 29, thus holding the shell and balloon in position.

As stated above, the balloon is made of a very flexible and stretchable material which is preferably thin rubber sheeting. It may be pre-manufactured in suitable shape for attachment to the shell, or it may be in the form of plain sheeting bent and glued to the edges of the shell. It is filled with a liquid or gas such as water or air, preferably by means of a syringe. The needle of the syringe is inserted into the balloon through a hole on the shell (not shown) which is subsequently closed by glue or putty.

The jaws, and especially the shells, have been shown to be of semi-circular cross section, but it will be understood that a curvature different from, or similar to a semi-circle is likewise acceptable. As shown, the two balloons can be pressed onto the vessel or duct by hand pressure or by the force of a suitable spring.

On the other hand, it may be possible to make the jaws exchangeable, each jaw carrying a balloon fastened to it in one of the described manners, or in any other way. It is, for instance proposed that each exchangeable jaw includes a rigid sleeve which can be mounted on the end of a conventional forceps, with the balloons facing each other.

It will be understood that the manner of fastening the balloon to the jaw by means of a shell is not limited to the embodiments illustrated and described in the foregoing, but that other means of connection may be employed. The shells are not necessarily made of plastic but of any other suitable material necessitating other means of connection to the jaws.

In the description of FIGS. 1 and 2 above it was indicated that the clamp was formed by using a conventional forceps and altering its shape, but it is evident that the entire clamp and the concave jaw is preferably manufactured by forging each lever in a die with or without subsequent machining.

We claim:

1. A vascular clamp for occluding a blood vessel or duct, the vascular clamp comprising:

a pair of pivoting arms, each arm comprising a handle end and a distal end, each pivoting arm comprising a clamping jaw rigidly attached to the distal end thereof, the clamping jaw comprising a concave substantially semi-cylindrical chamber, the clamping jaws being movable between an open position and a closed position, the clamping jaws being aligned so as to form a substantially cylindrical chamber in the closed position;

a balloon mounted in the concave semi-cylindrical chamber of each clamping jaw, each balloon comprising a substantially semi-cylindrical rigid shell conforming to the concave semi-cylindrical chamber and a thin, elastic material pre-filled with a liquid or gaseous fluid at a predetermined pressure, the balloons being configured to completely surround and occlude the blood vessel or duct in the closed position of the vascular clamp; and means for attaching the rigid shell of each balloon to its associated clamping jaw.

2. The vascular clamp according to claim 1, wherein the pivoting arms cross each other and are connected by a pivot pin at their intersection point, the arms comprising grips at their handle ends.

3. The vascular clamp according to claim 1, wherein each pivoting arm is angled, the pivoting arms being pivotally connected at their respective vertices, the vascular clamp further comprising spring means positioned between the handle ends for pushing the handle ends apart and the distal ends together.

4. The vascular clamp according to claim 1, wherein each shell is constructed of a rigid plastic material.

5. The vascular clamp according to claim 1, wherein the balloon is constructed of rubber sheeting.

6. The vascular clamp according to claim 5, wherein the rubber sheeting is fastened to the shell by gluing so as to form the balloon.

7. The vascular clamp according to claim 1, wherein each jaw comprises a semi-cylindrical concave inner surface and a convex outer surface substantially parallel to the inner surface.

8. The vascular clamp according to claim 7, wherein the means for attaching the shells to the jaws comprises:

at least two strips protruding out of a convex side of the shell, each strip comprising a hole;

at least two perforations in each jaw with positions corresponding to the positions of the strips on the shell;

at least two outwardly protruding lugs on a convex side of each jaw, the strips being adapted to be pushed through the openings in the jaw, to be bent over onto an outer surface of the jaw and to engage one of the two lugs with the hole in the strip.

9. The vascular clamp according to claim 8, wherein the lugs are provided with enlarged bulbs at their outer ends to prevent the strips from freeing themselves from engagement with the lugs.

10. The vascular clamp according to claim 1, wherein the means for attaching each shell to its respective clamping jaw comprises:

two lugs protruding from the convex side of the shell each of the lugs being circularly recessed;

two perforations in the clamping jaw with positions corresponding to the positions of the lugs; and a lever rotatably mounted on a convex side of the clamping jaw, the lever comprises lateral recesses toward each end thereof, the lever being adapted to be swiveled until the lateral recesses engage with the circular recesses in the lugs.

11. The vascular clamp according to claim 1, wherein the clamping jaws are releasably attached to the ends of conventional forceps.

* * * * *